(12) United States Patent
Cooper et al.

(10) Patent No.: US 11,397,177 B2
(45) Date of Patent: Jul. 26, 2022

(54) DETECTION OF BIOMARKERS FROM EXHALED BREATH

(71) Applicant: The Regents of The University of California, Oakland, CA (US)

(72) Inventors: Dan M. Cooper, Orange, CA (US); Eric O. Potma, Irvine, CA (US); Kim Lu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 29 days.

(21) Appl. No.: 15/931,286

(22) Filed: May 13, 2020

(65) Prior Publication Data
US 2021/0063380 A1 Mar. 4, 2021

Related U.S. Application Data

(60) Provisional application No. 62/847,704, filed on May 14, 2019.

(51) Int. Cl.
| | |
|---|---|
| *G01N 33/497* | (2006.01) |
| *G01N 21/17* | (2006.01) |
| *A61B 5/08* | (2006.01) |
| *A61B 5/00* | (2006.01) |
| *A61B 10/00* | (2006.01) |

(52) U.S. Cl.
CPC ............ *G01N 33/497* (2013.01); *A61B 5/082* (2013.01); *A61B 5/4848* (2013.01); *G01N 21/1702* (2013.01); *A61B 2010/0087* (2013.01); *G01N 2021/1704* (2013.01); *G01N 2033/4975* (2013.01)

(58) Field of Classification Search
CPC ............ G01N 33/497; G01N 21/1702; G01N 2021/1704; G01N 2033/4975; A61B 5/082; A61B 2010/0087
See application file for complete search history.

(56) References Cited

U.S. PATENT DOCUMENTS

| | | | | |
|---|---|---|---|---|
| 2010/0020326 | A1* | 1/2010 | Van Kesteren | .... G01N 21/1702 356/437 |
| 2010/0027012 | A1* | 2/2010 | Fritz | .................. G01N 21/1702 356/432 |
| 2012/0183949 | A1* | 7/2012 | Hyde | ................... A61M 11/001 435/5 |
| 2012/0277612 | A1* | 11/2012 | Li | .......................... A61B 5/097 600/532 |
| 2013/0011872 | A1* | 1/2013 | Gabriel | ................ A61B 5/0813 435/34 |

FOREIGN PATENT DOCUMENTS

WO WO-2004029593 A1 * 4/2004 ........... H04R 23/008

* cited by examiner

*Primary Examiner* — Benjamin R Schmitt
(74) *Attorney, Agent, or Firm* — Gavrilovich, Dodd & Lindsey LLP

(57) ABSTRACT

The technology relates to devices and methods thereof for the detection of one or more biomarkers from a user's exhaled breath. In one embodiment, the present invention provides a device comprising a metered dose inhaler, and a sensor that detects one or more biomarkers comprising HFA, $CO_2$, and NO. In another embodiment, the device detects HFA, $CO_2$ and NO simultaneously by photoacoustic spectroscopy. In another embodiment, the device may be used as part of an overall treatment regimen for asthma or COPD.

15 Claims, 2 Drawing Sheets

DETECTION OF BIOMARKERS FROM EXHALED BREATH

CROSS-REFERENCE TO RELATED APPLICATIONS

The present application claims the benefit of priority under 35 U.S.C. § 119(e) of provisional application Ser. No. 62/847,704, filed May 14, 2019, the contents of which are hereby incorporated by reference.

FIELD OF THE INVENTION

The present disclosure relates to the medical field, and more specifically, medical devices for monitoring and enhancing treatment of asthma and COPD.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Asthma and COPD (chronic obstructive pulmonary disease) are among the top 6 causes of death in the world. These deaths are prevalent in part because asthma management and the efficacy of metered dose inhalers are insufficient. Physicians must make treatment decisions, like whether to step up or step down in treatment, based upon estimates and projections. There is little real data to refer to when determining the dosage to be prescribed. Asthma and COPD patients often do not know how much of the drug they have inhaled and therefore cannot accurately communicate their dosages to their physicians.

Current solutions to this problem include attachable sensors to metered dose inhalers that record how many times a patient depresses the inhaler's canister and send the data to a physician. Some inhalers have dosage counters that keep track of how many times the canister is pressed. Some physicians weigh inhaler canisters to know how much of the drug has been used. Another solution that is implemented is sending asthma and COPD educators to teach patients how to correctly take their inhalers. However, the only primary way to detect the concentration of the drug in the patient's body is through blood measures of the circulating levels of active medication.

The current solutions to this problem do not accurately address the issue. Most of the current solutions do not actually measure the amount of medication inhaled by the patient, but instead only measure the amount of medication that has left the canister. This medication could have been sprayed into the air, or escaped from the patient's mouth due to a poor seal between the mouthpiece and the patient's lips, for example. It may take several weeks to obtain the results of the blood measurements of the active medication, invaluable as physicians need real-time accurate results at the point-of-care.

Thus, there is a need in the art for novel and more effective devices and methods of detection of gases from exhaled breath, including for better management of asthma and efficacy of metered dose inhalers.

SUMMARY OF THE INVENTION

Various embodiments include a device, comprising a sensor that detects one or more biomarkers from a user's exhaled breath by photoacoustic spectroscopy (PAS). In another embodiment, the device is used in combination with a metered dose inhaler. In another embodiment, the one or more biomarkers comprises an aerosol. In another embodiment, the one or more biomarkers comprise HFA, $CO_2$, and/or NO. In another embodiment, the sensor comprises a triple PAS gas sensor. In another embodiment, the sensor comprises the following components operably linked: a light source, a filter, a modulator, a detection chamber, a sound detector, and a spectrum analyzer. In another embodiment, the light source is an IR light source. In another embodiment, the filter is a three-fold filter. In another embodiment, the modulator is a three-fold modulator. In another embodiment, the sound detector is a microphone detector. In another embodiment, the device uses a tube to guide the user's exhaled breath to the sensor. In another embodiment, the device is used in conjunction with an overall treatment regimen of a pulmonary disease. In another embodiment, the pulmonary disease is asthma. In another embodiment, the pulmonary disease is chronic obstructive pulmonary disease (COPD). In another embodiment, the device provides a determination of what is the level of a drug that has been received by the user from the user's exhaled breath. In another embodiment, the device provides a reading in a few seconds of the effectiveness of administration of a drug administered to the user. In another embodiment, the device is described in FIG. 1 herein.

Other embodiments include a method of treating a pulmonary disease in a subject, comprising providing a device comprising a metered dose inhaler and a sensor that detects one or more biomarkers from a user's exhaled breath, and treating the pulmonary disease in the subject. In another embodiment, the biomarkers comprise HFA, $CO_2$, and/or NO. In another embodiment, the device detects one or more biomarkers by photoacoustic spectroscopy. In another embodiment, the device detects one or more biomarkers by measuring the concentration of matter given by acoustic waves produced by the exposure of matter to light. In another embodiment, the sensor comprises a chamber, a light source, a light filter, a light modulator, a microphone detector, and/or a spectrum analyzer. In another embodiment, the pulmonary disease is asthma. In another embodiment, the pulmonary disease is chronic obstructive pulmonary disease (COPD).

Other embodiments include a method of increasing the effectiveness of measurement of active medication being administered to a patient, comprising providing a patient being currently treated by medication, and managing the efficacy of the medication being administered by using a device comprising a metered dose inhaler and a sensor that detects one or more biomarkers from a user's exhaled breath. In another embodiment, the biomarkers comprise HFA, $CO_2$, and/or NO. In another embodiment, the device detects one or more biomarkers by photoacoustic spectroscopy. In another embodiment, the device provides noninvasive detection of the levels of the medication from the user's exhaled breath to provide real time accurate readings of treatment effectiveness.

Other features and advantages of the invention will become apparent from the following detailed description, taken in conjunction with the accompanying drawings, which illustrate, by way of example, various embodiments of the invention.

DETAILED DESCRIPTION

Figure 1:
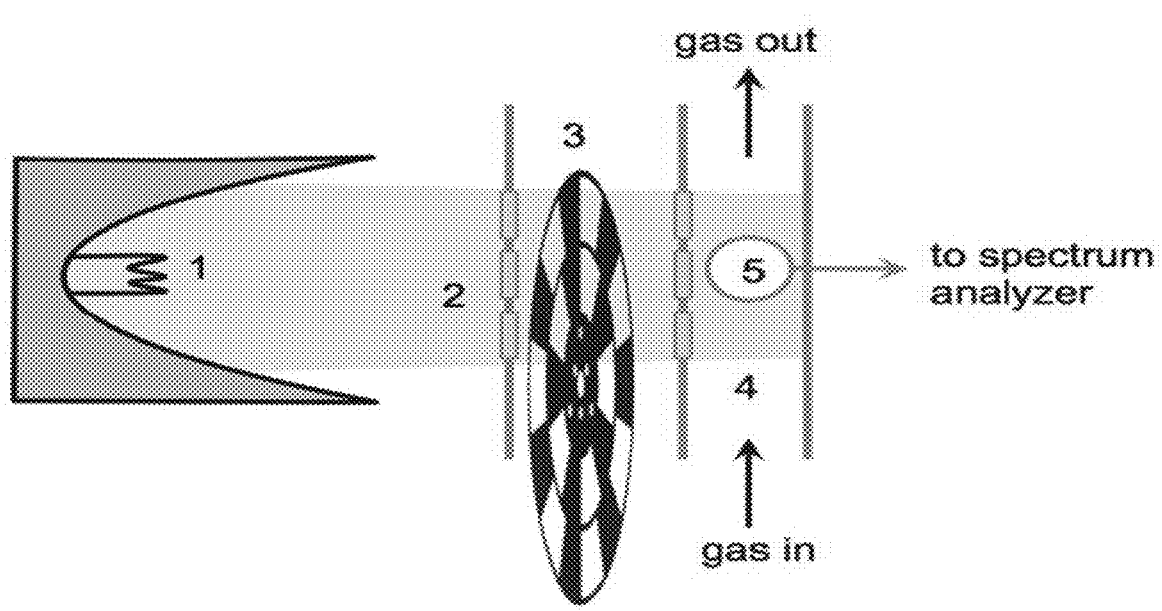
FIG. 1 depicts, in accordance with embodiments herein, a schematic of a sensor. In one embodiment the sensor is a triple PAS gas sensor. As referenced herein, FIG. 1 describes a Light Source 101, Filter 102, Modulator 103, Detection Chamber 104, Sound Detector 105 and a Spectrum Analyzer 106. In one embodiment, the Light Source 101 is an IR light source. In another embodiment, the Filter 102 is a three-fold filter. In another embodiment, the Modulator 103 is a three-fold modulator. In another embodiment, the Sound Detector 105 is a microphone detector.
Figure 2:
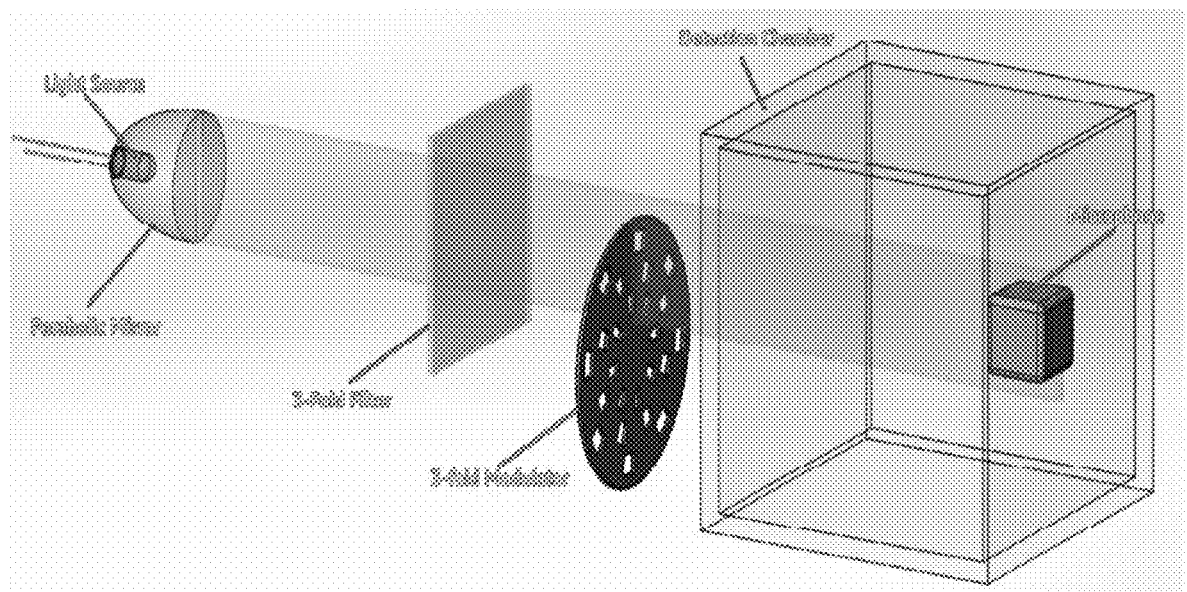
FIG. 2 depicts, in accordance with embodiments herein, a schematic of a sensor, such as a triple PAS gas sensor. As referenced herein, FIG. 2 describes a Light Source 101, Filter 102, Modulator 103, Detection Chamber 104, Sound Detector 105 and a Spectrum Analyzer 106. In one embodiment, the Light Source 101 is an IR light source. In another embodiment, the Filter 102 is a three-fold filter. In another embodiment, the Modulator 103 is a three-fold modulator. In another embodiment, the Sound Detector 105 is a microphone detector.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the abbreviation of "PAS," refers to photoacoustic spectroscopy.

As used herein, the term "COPD" refers to chronic obstructive pulmonary disease.

As used herein, the abbreviation of "$CO_2$" refers to carbon dioxide.

As used herein, the abbreviation "NO," refers to nitrogen monoxide.

As used herein, the propellant 1,1,1,2-tetrafluoroethane is also referred to by the abbreviation "HFA."

As further described herein, metered dose inhalers are often the first line therapy in treating pulmonary diseases such as asthma and COPD (chronic obstructive pulmonary disease), with the drug delivered via an aerosol most commonly known as HFA. This propellant, along with $CO_2$ and NO (nitric oxide), can rapidly be detected from a patient's exhaled breath, which can provide valuable information on the delivery of inhaled medications. The device detects biomarkers HFA, $CO_2$, and NO using photoacoustic spectroscopy, which measures the concentration of matter given by the acoustic waves produced by the exposure of the matter to light.

In one embodiment, the present invention provides a device comprising a metered dose inhaler, and a sensor that detects one or more biomarkers from a user's exhaled breath. In another embodiment, the biomarkers comprise HFA, $CO_2$, and/or NO. In another embodiment, the device detects HFA, $CO_2$ and NO simultaneously. In another embodiment, the device measures the amount and/or analyzes each of the biomarkers. In another embodiment, the device detects one or more biomarkers by photoacoustic spectroscopy. In another embodiment, the device detects one or more biomarkers by measuring the concentration of matter given by acoustic waves produced by the exposure of matter to light.

In another embodiment, the present invention provides a device wherein exhaled gases are guided through a tube to a sensor. In another embodiment, the sensor comprises a Light Source 101, Filter 102, Modulator 103, Detection Chamber 104, Sound Detector 105 and/or a Spectrum Analyzer 106. In another embodiment, the Light Source 101 is an IR light source. In another embodiment, the Filter 102 is a three-fold filter. In another embodiment, the Modulator 103 is a three-fold modulator. In another embodiment, the Sound Detector 105 is a microphone detector.

In another embodiment, the device is described in FIG. 1 herein. In accordance with various embodiments herein, a sample enters the Detection Chamber 104 where it is exposed to a Light Source 101. In another embodiment, the absorption of the light by each of the gases is analyzed and the concentration of each gas in the sample is detected. In another embodiment, this information could then be analyzed and sent to a cloud, where a physician, for example, can access patient specific results and determine the appropriate treatment given the amount of HFA, $CO_2$, and NO present in the patient's exhaled breath. In another embodiment, the levels of HFA detected from the breath will correspond to when and how effectively the patient adhered to a recommended schedule of medication use, as there is a direct correlation between HFA and the drug in the metered dose inhalers. In another embodiment, the device will allow for proper training of inhaled medications to ensure effective administration.

As further described herein, the inventors tried to be conscious of design criteria of a sensor that included factors such as detection sensitivity, the speed of detection, robustness and portability. In one embodiment, to provide greater detection sensitivity, speed of detection, robustness and portability, the device comprises a sensor based on the principle of photoacoustic spectroscopy (PAS). In one embodiment, the device is specifically tailored for rapid and reliable quantitative analysis of the three target gases in breath, namely HFA, NO, and $CO_2$. In another embodiment, the device is compact and portable, and/or suitable for clinical use.

As further described herein, the PAS principle is based on the absorption of IR (infrared) radiation by molecular substances. Many gases have unique molecular bond vibrations, called vibrational modes, which carry a characteristic frequency, and these modes can be excited at specific IR wavelengths. In PAS, the energy absorbed by the molecules produces a local change in temperature of the gas, which produces a difference in pressure. In case the IR radiation is temporally modulated, the absorbed energy is translated into a pressure modulation. This pressure modulation can be detected with a microphone. In this fashion, dependent on the gas, very high detection sensitivities can be reached down to $10^{-3}$ parts per million (ppm).

In accordance with various embodiments herein, for a device that detects gases simultaneously, such as the three target gases $CO_2$, HFA, and NO simultaneously, three specific vibrational features may be distinguished. In one embodiment, for a device to detect $CO_2$, one may select the ~2350 $cm^{-1}$ symmetric stretching mode. In another embodiment, the device identifies NO through the stretching mode near 1920 $cm^{-1}$. In another embodiment, HFA can be probed through the unique C-F vibrational mode near 1230 $cm^{-1}$. In another embodiment, all modes can be excited simultaneously (broadband excitation). In another embodiment, to detect the absorption of light at each of these vibrational frequencies separately, one may modulate the light at each of these three frequencies. In another embodiment, the signal from a microphone is then filtered at each of the modulation frequencies. In another embodiment, the detected amplitude in each of the demodulated frequency channels is then directly proportional to the concentration of each of the three target gases.

As also described in FIG. 1 herein, in one embodiment, the device includes a sensor that includes a Light Source 101, Filter 102, Modulator 103, Detection Chamber 104, Sound Detector 105 and a Spectrum Analyzer 106. In one embodiment, the Light Source 101 is an IR light source. In another embodiment, the Filter 102 is a three-fold filter. In another embodiment, the Modulator 103 is a three-fold modulator. In another embodiment, the Sound Detector 105 is a microphone detector. In one embodiment, the light source is an incandescent filament, producing light in the 2500-1000 $cm^{-1}$ range to efficiently excite the target molecules. In another embodiment, the filament is mounted on a parabolic reflector for efficiently directing the light towards the detection chamber. In another embodiment, the light filter is a three-fold filter, where the IR radiation passes through a filter that is composed of three adjacent parts, with one part of the filter passes narrow band radiation in the 2300-2400 $cm^{-1}$ range, a second part in the 1900-1950 $cm^{-1}$ range, and a third part in the 1200-1260 $cm^{-1}$ range. The narrower the filter, the better the specificity. In another embodiment, custom-designed, thin film dielectric coatings are used. In another embodiment, light modulator comprises a spinning wheel, which contains three slotted rings. In another embodiment, when the spinning wheel is spun, the slots produce three different frequencies in the 200-500 Hz range. In another embodiment, each slot passes one of the three narrowband IR excitation windows, with the width of each window about 5 mm. In another embodiment, the detection chamber comprises a tube-shaped compartment directly connected to the gas inlet tube, where light passes through calcium fluoride windows into the detection chamber. In another embodiment, the width of the tube is 5 to 10 mm. In another embodiment, the microphone detector is mounted at a 90 degree angle relative to the propagation direction of the light, and directly faces the gas in the detection chamber. In another embodiment, the spectrum analyzer and/or demodulator comprises an apparatus that analyzes the microphone signal converted to a voltage. In another embodiment, the apparatus digitizes the time-varying voltage signal, and performs digital Fast Fourier transformation on a computer. In another embodiment, the spectral content of the signal can then be displayed at a refresh rate of at least 1 second per frame, with the magnitude at each of the three modulation frequencies is determined and converted into a gas concentration. In another embodiment, the gas concentrations are shown on a display at a refresh rate of once per second.

In accordance with various embodiments herein, a drug, or active medication, may be administered to a user through an inhaler, such as a metered dose inhaler for example, or as a spray. The administration of the drug, or active medication, in accordance with various embodiments herein, may also be in conjunction with a sensor that detects one or more biomarkers from the user's breath. For example, in one embodiment, the present invention provides a composition that includes medication for the treatment of asthma, or COPD, or a combination thereof for example, formulated to be applied to a user as a medicinal inhalant or spray. In one embodiment, the composition comprises a drug or combination of drugs as an aerosol, or a solution or suspension in a vehicle optionally containing a polymer or combination of polymers. The compositions of the invention preferably comprise up to about 30% of at least one medicament (e.g., 0.0001% to about 30%), more preferably up to about 10% of at least one medicament (e.g., 0.0001% to about 10%) and most preferably up to about 5% of at least one medicament (e.g., 0.0001% to about 5%) dissolved or suspended in one or more vehicles which comprise up to 90% of the composition (e.g., 0.0001% to about 90%). The exact formulation of the composition may vary depending on the nature of the particular medicament used (for example, the solubility profile) and the release profile desired. The compositions can be dispensed from any dispenser or inhaler or delivery device, and is in no way limited to a metered dose inhaler, for example. The drug from the composition may also be released over a period of time, or in other embodiments, immediately.

In another embodiment, the invention also provides a method of preparing a dispenser, or inhaler or spray, containing various compositions of the invention comprising mixing the ingredients of the composition with or without liquid propellant and placing the mixed ingredients in the dispenser, inhaler or spray. Similarly, in another embodiment, the invention provides a method of preparing an aerosol dispenser containing a spray composition of the invention comprising mixing the ingredients of the composition without propellant and charging the mixture together with propellant into an aerosol dispenser. In another embodiment, the composition is preferably dispensed from the chosen inhaler, dispenser or spray in a metered dose. The medicament can be any medicinal compound in the salt or base form or a combination of compounds which is stable on mixing with the other ingredients of the composition and effective on administration.

In another embodiment, the present invention provides a method of treating a pulmonary disease comprising providing a device comprising a metered dose inhaler and a sensor that detects one or more biomarkers from a user's exhaled breath, and treating the pulmonary disease. In another embodiment, the biomarkers comprise HFA, $CO_2$, and/or NO. In another embodiment, the device detects one or more biomarkers by photoacoustic spectroscopy.

In another embodiment, the present invention provides a method of treating asthma and/or chronic obstructive pulmonary disease (COPD) in a patient by providing a device comprising a metered dose inhaler and a sensor that detects one or more biomarkers from a user's exhaled breath, and treating the asthma and/or COPD in the patient by managing the efficacy and effective medication dosages of the metered dose inhaler. In another embodiment, the biomarkers comprise HFA, $CO_2$, and/or NO. In another embodiment, the device detects one or more biomarkers by photoacoustic spectroscopy.

In another embodiment, the present invention provides a method of measuring levels of active medication in a patient, by providing a device comprising a metered dose inhaler and a sensor that detects one or more biomarkers from a user's exhaled breath, and measuring the level of active medication administered to the patient. In another embodiment, the active medication is for the treatment of a pulmonary disease. In another embodiment, the active medication is for treatment of asthma and/or COPD. In another embodiment, the biomarkers comprise HFA, $CO_2$, and/or NO.

In another embodiment, the present invention provides a method of increasing the effectiveness of measurement of active medication being administered to a patient, comprising providing a patient being treated by medication, and managing the efficacy of the medication by using a device comprising a metered dose inhaler and a sensor that detects one or more biomarkers from a user's exhaled breath. In another embodiment, the biomarkers comprise HFA, $CO_2$, and/or NO.

EXAMPLES

Example 1

Generally

Metered dose inhalers are the first line therapy in treating pulmonary diseases such as asthma and COPD (chronic obstructive pulmonary disease). The drug is delivered via an aerosol most commonly known as HFA. This propellant, along with $CO_2$ and NO (nitric oxide), can rapidly be detected from a patient's exhaled breath, which can provide valuable information on the delivery of inhaled medications. The device detects biomarkers HFA, $CO_2$, and NO using photoacoustic spectroscopy, which measures the concentration of matter given by the acoustic waves produced by the exposure of the matter to light. The device consists of a chamber, light source, light filter, light modulator, microphone detector, and spectrum analyzer. The sample enters the chamber where it is exposed to a light source. The absorption of the light by each of the gases is analyzed and the concentration of each gas in the sample is detected. This information could then be analyzed and sent to a cloud, where the physician can access patient specific results and determine the appropriate treatment given the amount of HFA, $CO_2$, and NO present in the patient's exhaled breath. The levels of HFA detected from the breath correspond to when and how effectively the patient adhered to the recommended schedule of medication use, as there is a direct correlation between HFA and the drug in the metered dose inhalers. This device will also allow for proper training of inhaled medications to ensure effective administration.

Detecting exhaled gases quickly and reliably can have a major impact on the efficacy of administering pulmonary drugs through respiratory gas intake. A rapid detection of carbon dioxide ($CO_2$), nitrogen monoxide (NO), as well as registration of the propellant 1,1,1,2-tetrafluoroethane (here abbreviated as HFA) in exhaled gas is helpful in determining the delivery of inhaled gas. For this purpose, the inventors developed a sensor that enables the simultaneous detection of $CO_2$, nitrogen monoxide NO, and HFA.

Some of the design criteria of the sensor include the detection sensitivity, the speed of detection, robustness and portability. To meet these criteria, the inventors developed a sensor based on the principle of photoacoustic spectroscopy (PAS). PAS detectors have been successful in detecting a variety of gases with a detection sensitivity relevant to the anticipated ranges for breath analysis; however, not for the measurement of the three target gases as it pertains to breath analysis. Various embodiments herein describe a device specifically tailored for rapid and reliable quantitative analysis of the three target gases in breath. In one embodiment, the device is compact and portable and suitable for clinical use.

The PAS principle is based on the absorption of IR (infrared) radiation by molecular substances. Many gases have unique molecular bond vibrations, called vibrational modes, which carry a characteristic frequency. These modes can be excited at specific IR wavelengths. Conventional IR spectroscopy uses a photodetector to determine the loss of light due to the absorption by molecules. Although useful in analytical laboratories, this method of detection is not sensitive enough for the rapid detection of gases. PAS uses a different detection mechanism. The energy absorbed by the molecules produces a local change in temperature of the gas, which produces a difference in pressure. In case the IR radiation is temporally modulated, the absorbed energy is translated into a pressure modulation. This pressure modulation can be detected with a microphone. In this fashion, dependent on the gas, very high detection sensitivities can be reached down to $10^{-3}$ parts per million (ppm).

To detect the three target gases simultaneously, three specific vibrational features should be distinguished. To detect $CO_2$, the inventors selected the ~2350 $cm^{-1}$ symmetric stretching mode. NO can be identified through the stretching mode near 1920 $cm^{-1}$, and HFA can be probed through the unique C-F vibrational mode near 1230 $cm^{-1}$. All modes can be excited simultaneously (broadband excitation). The challenge is to detect the absorption of light at each of these vibrational frequencies separately, and the inventors accomplished this by modulating the light at each of these three frequencies. The signal from the microphone is then filtered at each of the modulation frequencies. The detected amplitude in each of the demodulated frequency channels is then directly proportional to the concentration of each of the three target gases.

In one embodiment, the exhaled gases are guided through a tube to the sensor. In one embodiment, the sensor is made of six parts: 1) an IR light source, 2) a three-fold filter, 3) a three-fold modulator, 4) a detection chamber, 5) a microphone detector, and 6) a spectrum analyzer. A schematic of an example of the sensor is shown in FIG. 1 herein.

Example 2

Detailed Description of FIG. 1 Herein

Description of the parts.
1) Light source. The simplest light source is an incandescent filament. This produces sufficient light in the 2500-1000 $cm^{-1}$ range to efficiently excite the target molecules. The filament is mounted on a parabolic reflector for efficiently directing the light towards the detection chamber.
2) Three-fold filter. The IR radiation passes through a filter that is composed of three adjacent parts. One part of the filter passes narrow band radiation in the 2300-2400 $cm^{-1}$ range, a second part in the 1900-1950 $cm^{-1}$ range and a third part in the 1200-1260 $cm^{-1}$ range. The narrower the filter, the better the specificity. These filters are one of the most critical parts of the device. For this purpose, custom-designed, thin film dielectric coatings are used.

3) Three-fold modulator. The modulator consists of a spinning wheel, which contains three slotted rings. When spun, the slots produce three different frequencies in the 200-500 Hz range. Each slot passes one of the three narrowband IR excitation windows. The width of each window is about 5 mm.

4) Detection chamber. The light passes through calcium fluoride windows into the detection chamber, which consists of a tube-shaped compartment directly connected to the gas inlet tube. The width of the tube is 5 to 10 mm.

5) Microphone detector. The microphone detector is mounted at a 90 degree angle relative to the propagation direction of the light, and directly faces the gas in the detection chamber.

6) Spectrum analyzer/demodulator. The microphone signal, converted to a voltage, is analyzed by a spectrum analyzer. One implementation digitizes the time-varying voltage signal, and performs digital Fast Fourier transformation on a computer. The spectral content of the signal can then be displayed at a refresh rate of at least 1 second per frame. The magnitude at each of the three modulation frequencies is determined and converted into a gas concentration. The gas concentrations are shown on a display at a refresh rate of once per second.

Example 3

Some Advantages

Some disadvantages and limitations of the methods currently used to detect inhaler efficacy in patients are overcome by various embodiments herein. Most current methods do not actually measure the concentration of the medication inhaled. They instead measure the amount of medication that has left the canister, even the medication that dissipates into the ambient air. Blood measurements of the medication are invasive and time consuming. Various embodiments herein are more efficient than current methods and devices, as it can noninvasively detect the levels of the drug from exhaled breath in seconds and provide real-time accurate readings, something highly valued in the medical field.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps, some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A device, comprising:
   a sensor that detects a plurality of biomarkers from a user's exhaled breath by photoacoustic spectroscopy (PAS), wherein the sensor comprises:
   a broadband light source;
   a multi-light filter, wherein the multi-light filter filters the light produced from the broadband light source into a plurality of narrow-band light ranges, wherein the narrow-band light ranges are configured to excite specific vibrational features for each of the plurality of biomarkers; and
   a modulator, wherein the modulator is configured to modulate each of the plurality of narrow-band light ranges to have a frequency in the 200-500 Hz range, wherein the frequency of each of the plurality of narrow-band light ranges is different,
   wherein the plurality of biomarkers comprise HFA, $CO_2$ and NO, and wherein the sensor detects the plurality of biomarkers simultaneously.

2. The device of claim 1, wherein the plurality of biomarkers includes HFA.

3. The device of claim 1, wherein the plurality of biomarkers comprises an aerosol.

4. The device of claim 1, wherein the sensor further comprises:
   a detection chamber;
   a sound detector; and
   a spectrum analyzer.

5. The device of claim 4, wherein the sound detector is a microphone detector, and wherein the microphone detector generates a voltage signal that is processed by the spectrum analyzer.

6. The device of claim 5, wherein the signal generated by the microphone detector is filtered at each of frequencies in the 200-500 Hz range in which the plurality of narrow-band light ranges have been modulated.

7. The device of claim 5, wherein the microphone detector is mounted at a 90 degree angle relative to the propagation direction of the light and faces the gas in the detection chamber.

8. The device of claim 4, wherein the device comprises a tube to guide the user's exhaled breath to the detection chamber of the sensor.

9. The device of claim 8, wherein the detection chamber comprises calcium fluoride windows to allow passage of light.

10. The device of claim 1, wherein the broadband light source produces light in the 2500-1000 $cm^{-1}$ range.

11. The device of claim 1, wherein the multi-part filter filters light produced from the broadband light source into narrow-band light ranges selected from 2300-2400 $cm^{-1}$, 1900-1950 $cm^{-1}$, and 1200-1260 $cm^{-1}$.

12. The device of claim 1, wherein the modulator comprises a spinning wheel which contains a plurality of slotted rings.

13. The device of claim 12, wherein each slotted ring of the plurality of slotted rings is configured to allow passage of only one of the plurality of narrow-band light ranges, and wherein each slotted ring allows passage of a different narrow-band light range.

14. The device of claim 12, wherein each slotted ring of the plurality of slotted rings produces a different frequency in the 200-500 Hz range when the wheel is spun.

15. The device of claim 1, wherein the sensor is capable of detecting the levels of the plurality of biomarkers from a user's exhaled breath in a few seconds.

* * * * *